United States Patent [19]

Brown

[11] Patent Number: 5,026,390
[45] Date of Patent: Jun. 25, 1991

[54] SURGICAL STAPLE

[76] Inventor: Alan W. Brown, 4 Hartley Cir., Apt. 824, Owing Mills, Md. 21117

[21] Appl. No.: 587,830

[22] Filed: Sep. 20, 1990

Related U.S. Application Data

[62] Division of Ser. No. 426,373, Oct. 26, 1989.

[51] Int. Cl.$^5$ ............................................. A61B 17/00
[52] U.S. Cl. ................................... 606/221; 411/457; 411/483; 411/920
[58] Field of Search ............... 606/221; 411/456, 457, 411/483, 920, 921

[56] References Cited

U.S. PATENT DOCUMENTS

| | | | |
|---|---|---|---|
| 816,026 | 3/1906 | Meier | 606/221 |
| 1,123,290 | 1/1915 | Von Herff | 606/221 |
| 2,684,070 | 7/1954 | Kelsey | 606/221 |
| 2,817,339 | 12/1957 | Sullivan | 606/221 |
| 3,939,828 | 2/1976 | Mohr et al. | 606/221 |

Primary Examiner—Stephen C. Pellegrino
Assistant Examiner—Gary Jackson
Attorney, Agent, or Firm—Diller, Ramik & Wight

[57] ABSTRACT

A surgical staple is made from highly flexible material and has at least two piercing projections or points spaced from each other a first predetermined linear distance in a generally unstressed, neutral and inoperative condition of the staple. The staple is stressed in a selected fashion causing the piercing projections to be spaced from each other a second predetermined linear distance greater than the first predetermined linear distance. While the piercing projections are spaced from each other, the second predetermined linear distance under the induced forces, the staple is implanted by penetrating the skin with the piercing projections at opposite sides of an associated wound or incision. The forces are then removed from the surgical staple which inherently rebounds to its generally unstressed condition which in turn automatically draws opposite margins of the wound toward each other.

12 Claims, 3 Drawing Sheets

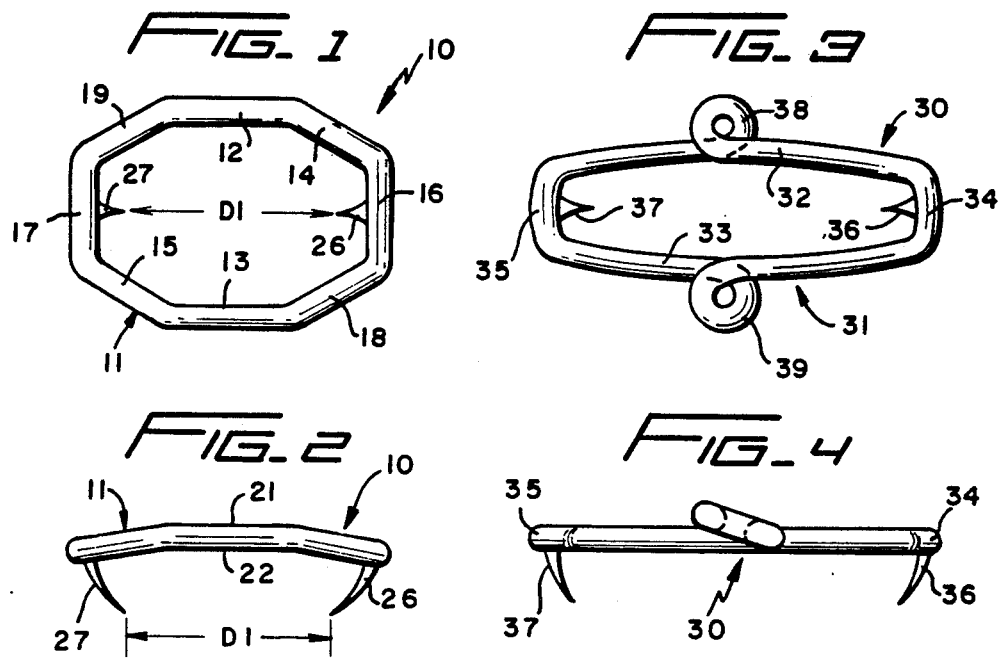
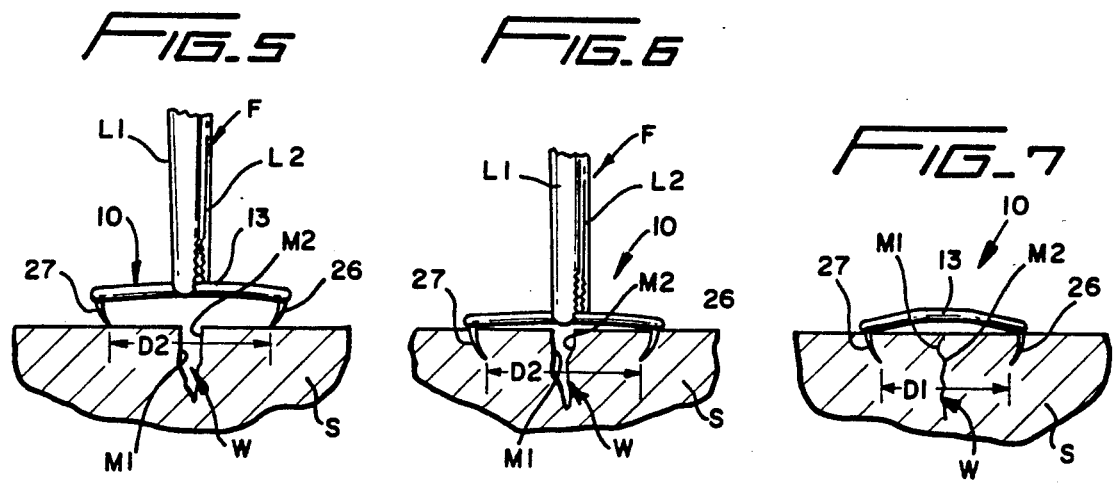

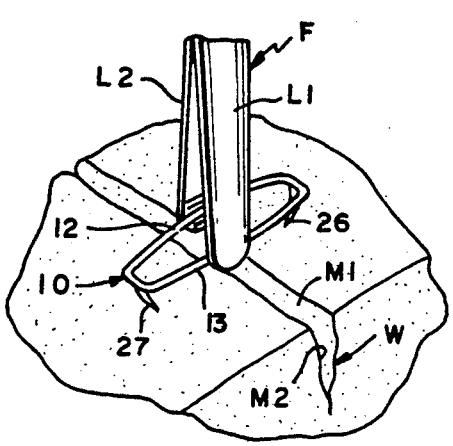
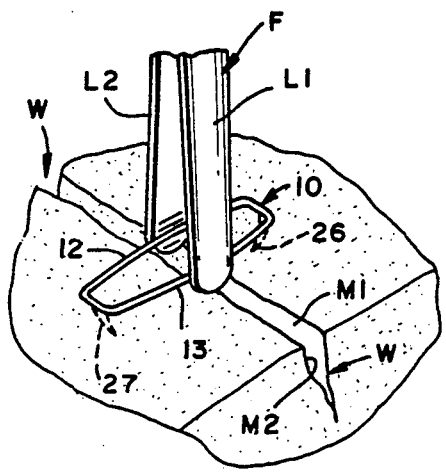
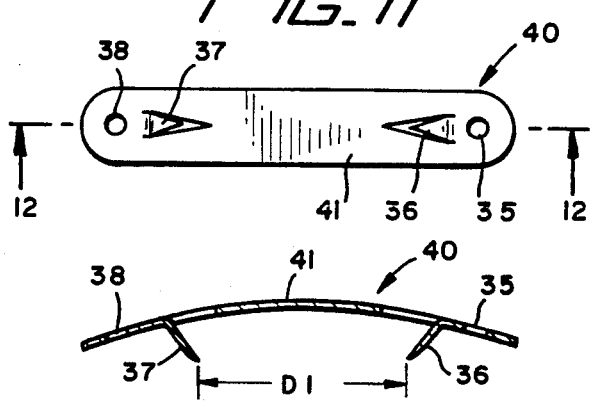
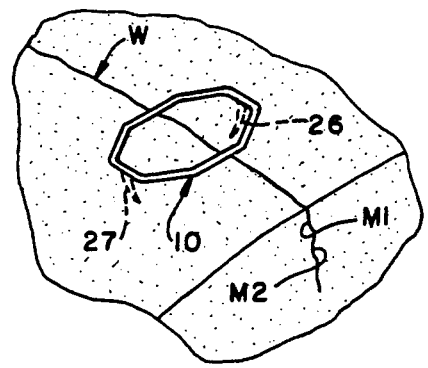
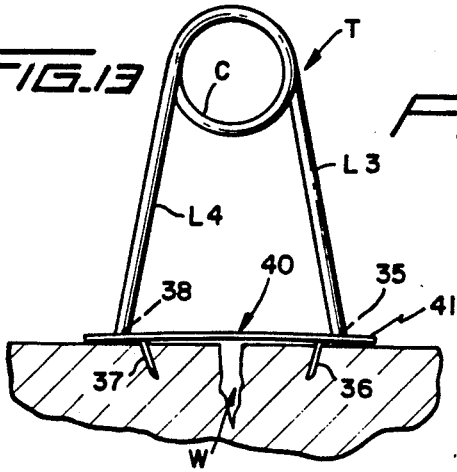
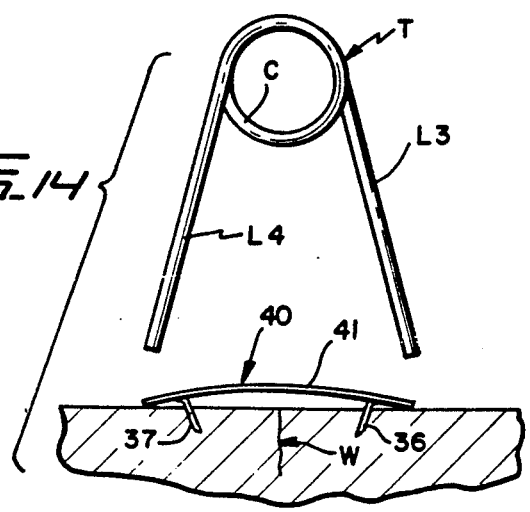

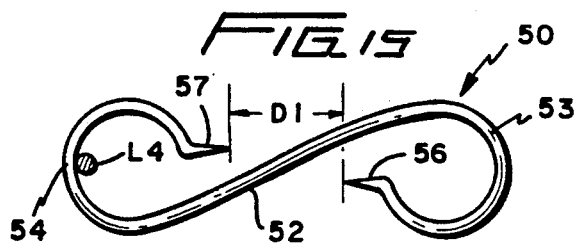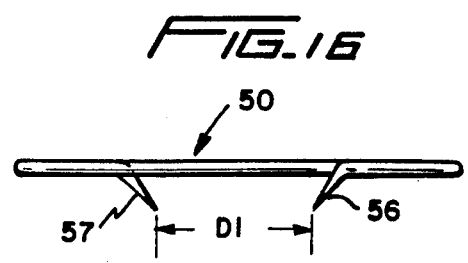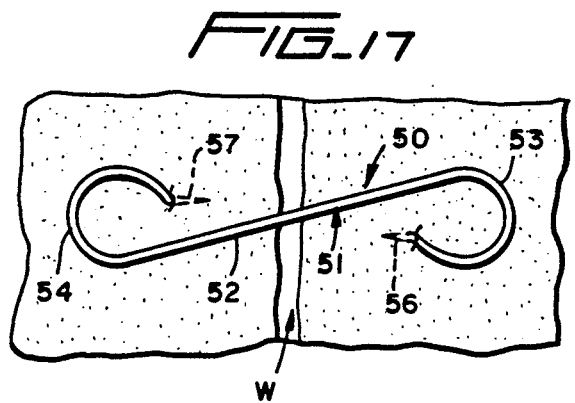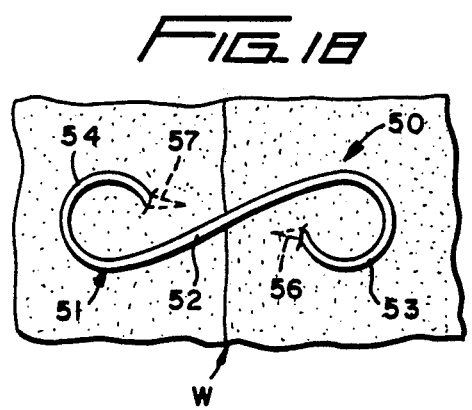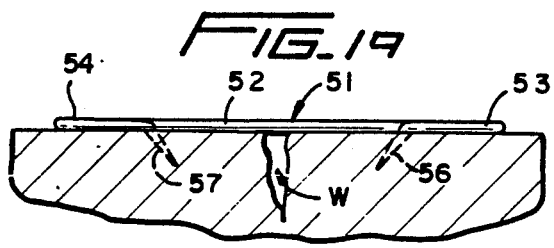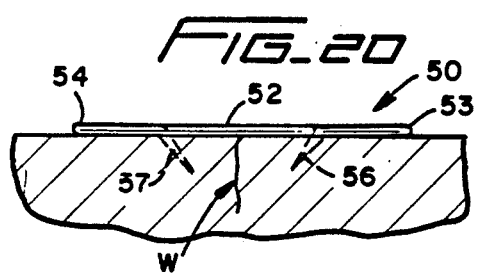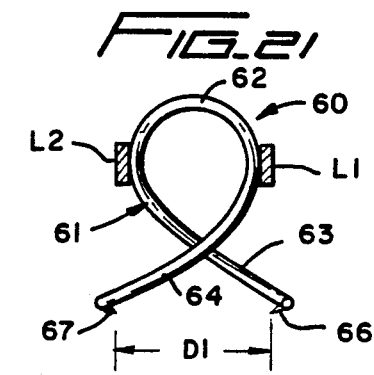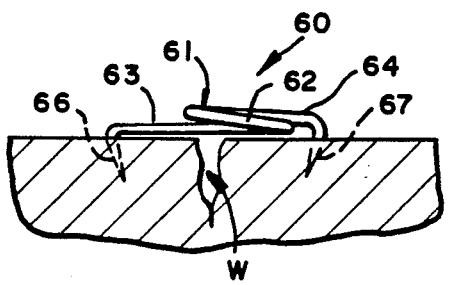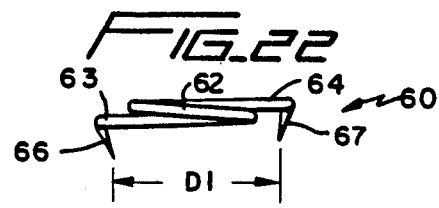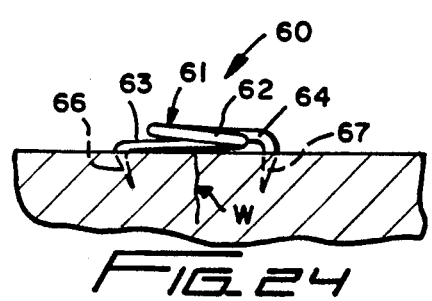

SURGICAL STAPLE

This application is a division of application Ser. No. 07/426,373, filed Oct. 26, 1989, now pending.

Another conventional surgical staple includes a generally U-shaped fastening member having legs which are received in two bores of a receiver member. An example of this type of surgical staple is found in U.S. Pat. No. 4,534,350. This type surgical staple is limited by the need to grasp the members both above and below the tissue plate.

A third surgical staple involves an open circular-shaped member, which when closed, has its free ends laterally disposed with respect to each other forming a split-ring configuration. Examples of this type of surgical staple are found in U.S. Pat. Nos. 2,881,762 and 4,595,007.

All known conventional surgical staples are limited by the inability or extreme difficulty in making adjustments in and to the tissue once the conventional surgical staples have been secured to the skin relative to an associated wound or incision. Generally, an unsatisfactorily placed surgical staple or clip must be removed using a separate removing device, the staple thus removed must be discarded and the discarded staple must then be replaced with a new staple This inconvenience is particularly troublesome in view of the limitation of such conventional staples to be placed or positioned accurately approximate the tissue margins. The stapling mechanisms associated with such conventional staples most often require an assistant to approximate the tissue margins and maintain these margins at a desired relative position while the surgeon operates the stapling mechanism to implant the staple. This method of utilizing two people for a single surgical staple implantation is inexact and leads to tissue deformation and misapproximation which renders this method inadequate for procedures requiring fine closure, as is found in ophthalamic or plastic surgery.

Conventional surgical staples as aforesaid are further limited by their general inability to provide varying degrees of tension in opposing tissue margins, or at least provide tension which can be controllably regulated by the surgeon during implantation. Once implanted, such staples cannot be altered in tension, either automatically as the wound heals or by the surgeon as might be necessary once tissue healing occurs. In other words once a staple is implanted at a particular tension and at a particular location to close the wound/incision or tissue, no further manipulation to increase or decrease this tension is possible. Furthermore, the lack of some type of tension adjustment in such conventional surgical staples also necessitates the use of long arcuate paths for the piercing members of these staples so that enough tissue is fixed to prevent subsequent loosening of the staple and the wound margin.

Finally, such conventional surgical staples are often limited in that their placement requires bulky stapling mechanisms which make visualization of the wound margins difficult. This disadvantage limits extremely small staples of this type for ophthalamic or plastic surgery.

SUMMARY OF THE INVENTION

The latter disadvantages of conventional surgical staples are overcome by a new surgical staple constructed from highly flexible material which has at least two piercing projections or points spaced from each other a first predetermined linear distance in a generally unstressed, neutral and inoperative condition of the staple. The staple is stressed in a selective fashion causing the piercing projections to be spaced from each other a second predetermined linear distance greater than the first predetermined linear distance. While the piercing projections are spaced from each other, the second predetermined linear distance under the induced forces, the staple is implanted by penetrating the skin with the piercing projections at opposite sides of an associated wound/incision. The forces are then removed from the surgical staple which inherently rebounds to its generally unstressed condition which in turn automatically draws opposite margins of the wound toward each other.

In keeping with the foregoing, the several novel surgical staples of the present invention can be easily placed in position and/or implanted with simple forceps or by utilizing a simple and small multiple stapling mechanism. The staples of the invention provide excellent visualization of the wound margins and can be both implanted and removed with the same simple forceps in a manner which does not adversely affect or destroy the staple allowing the same to be removed and reused to assure proper wound closure. The surgical staple is so constructed that the piercing projections or points can be simultaneously applied to the skin at opposite sides of the wound or first one and then the other of the piercing projections can be sequentially applied to opposite sides of the wound to effect implantation Irrespective of the method of application and implantation, the wound margins can be extremely precisely placed in opposition to each other to achieve desired would margin closure.

The novel surgical staples of the invention are also constructed of materials of varying flexibility and different configurations so as to allow variable wound margin tension depending upon the relative placement of the piercing projections relative to the wound margins. Thus, though the size, shape and curvature may vary, the surgical staples have the common characteristic that the piercing projections are spaced closer together in an unstressed, neutral operative condition than in a force-induced, stressed inoperative condition. It is in the force induced inoperative condition that the staples are applied to the skin, and when the stresses are relieved, the staples return to their unstressed neutral operative condition and in so doing, automatically close the wound and/or maintain the margins thereof closed.

With the above, and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a top plan view of a novel surgical staple constructed in accordance with this invention and illustrates the generally ring-like configuration thereof, and a pair of skin piercing projections projecting therefrom.

FIG. 2 is a side elevational view of the surgical staple of FIG. 1 and more clearly illustrates the configuration thereof, including the skin piercing projections FIG. 3 is a top plan view of another surgical staple, and illustrates the generally oval configuration thereof, and a pair of skin piercing projections projecting therefrom.

FIG. 4 is a side elevational view of the surgical staple of FIG. 3 and illustrates details thereof, including the skin piercing projections.

FIG. 5 is a fragmentary side elevational view of the surgical staple of FIGS. 1 and 2, and illustrates the staple being grasped by a pair of forceps which increase the distance between the projections prior to the projections being introduced into the skin adjacent the margin of a wound.

FIG. 6 is a fragmentary view similar to FIG. 5 and illustrates the surgical staple in spanning relationship to the margin of the wound with the piercing projections piercing the skin.

FIG. 7 is a fragmentary side elevational view of the staple of FIG. 6, and illustrates the manner in which the wound is closed upon the release of the force created by the forceps and the return of the staple to its original unstressed condition.

FIG. 8 is a fragmentary perspective view of the staple and forceps corresponding to the position illustrated in FIG. 5 and illustrates the manner in which the forceps induce a force in the staple to elongate the same and space the projections further away from each other than in the unstressed condition of FIGS. 1 and 2.

FIG. 9 is a fragmentary perspective view of the implantation of the staple corresponding to FIG. 6 and illustrates the piercing projections entering the skin while the staple is under the force-induced elongation of the forceps.

FIG. 10 is a fragmentary perspective view similar to FIG. 7 and illustrates the manner in which the wound margins are closed by the return of the surgical staple to its original unstressed condition (FIGS. 1 and 2) after the removal of the forceps.

FIG. 11 is a top plan view of another surgical staple, and illustrates a pair of depending projections and an opening adjacent each.

FIG. 12 is a cross sectional view taken generally along line 12—12 of FIG. 11, and illustrates the details of the curvature of the staple and the disposition of the projections relative thereto.

FIG. 13 is a fragmentary side elevational view of the staple of FIGS. 11 and 12 after being lengthened by a tool and implanted in spanning relationship to the margins of a wound.

FIG. 14 is a fragmentary side elevational view similar to FIG. 13, and illustrates the tool removed from the staple and the closing of the wound by the inherent return of the staple to its unstressed condition of FIGS. 11 and 12.

FIG. 15 is a top plan view of another surgical staple, and illustrates the generally S-shaped configuration thereof terminating in piercing projections.

FIG. 16 is a side elevational view, and illustrates the normal spacing or disposition of the projections of the staple of FIG. 15 relative to each other.

FIG. 17 illustrates the surgical staple of FIGS. 15 and 16 being first elongated and then implanted in bridging relationship to the margins of a wound by an appropriate tool.

FIG. 18 is a fragmentary top plan view similar to FIG. 17, and illustrates the manner in which the staple rebounds to its original configuration drawing the margins of the skin against each other to close the wound.

FIG. 19 is a fragmentary side view, and illustrates the manner in which the projections pierce the skin on opposite sides of the wound during the initial implantation as shown in FIG. 17.

FIG. 20 is a fragmentary side elevational view, and illustrates the final closing of the wound of FIG. 18.

FIG. 21 is a top plan view of another surgical staple, and illustrates the generally looped configuration thereof with the ends terminating in skin piercing projections.

FIG. 22 is a side elevational view of the surgical staple of FIG. 21

FIG. 23 illustrates the staple of FIG. 21 after the loop has been squeezed to increase the distance between the skin piercing projections and placing the same in bridging relationship to the wound.

FIG. 24 is a fragmentary elevational view similar to FIG. 23, but illustrates the staple returned to its unstressed condition closing the associated wound.

DESCRIPTION OF THE PREFERRED EMBODIMENTS

A novel surgical staple constructed in accordance with this invention is illustrated in FIGS. 1 and 2 of the drawings and is generally designated by the reference numeral 10.

The surgical staple 10 includes a generally uniplanar ring-like oval or O-shaped member 11 which is preferably constructed from resilient material possessing inherent spring-back characteristics, such as polymeric or copolymeric plastic material, stainless steel or the like, and can be resorbable material.

The member 11 includes opposite pairs of generally parallel portions 12, 14, 15; 16, 17; and 18, 19. Collectively, the portions 12-19 define the overall member or ring 11 including an uppermost surface 21 and an lowermost surface 22 (FIG. 2). The surfaces 21, 22 are in general parallelism to each other and are of a slight concavo-convex configuration such that the overall ring or member 11 opens slightly in a generally downward direction, as viewed in FIG. 2, but is generally uniplanar or flat, as is best seen in FIG. 2.

A pair of skin piercing projections 26, 27 project from the respective ring portions 16, 17 and in a direction generally away from the surfaces 21, 22 (FIG. 2) and at least partially toward each other. The skin piercing projections 26, 27 have relatively sharp skin piercing points (unnumbered).

The pair of skin piercing projections 26, 27 are spaced from each other a first predetermined linear distance D1 in the generally unstressed, neutral, operative condition of the surgical staple 10, but the projections 26, 27 can be spaced further from each other a second predetermined linear distance D2 (FIGS. 5, 6, 8 and 9) greater than the first predetermined linear distance D1 in a manner and for a purpose to be described immediately hereinafter.

Reference is made to FIGS. 5 and 8 of the drawings which diagrammatically illustrates skin S having a wound W defined by margins M1, M2. Forceps F having legs L1, L2 (FIG. 8) are used to grasp the surgical staple 10 specifically in spanning relationship to the portions 12, 13. When the forceps F are manipulated to move the legs L1, L2 toward each other, the portions 12, 13 of the ring member 11 similarly move toward each other and the portions 16, 17 move away from each other. In this fashion the unstressed distance D1 is lengthened to the distance D2 through the forces or stresses induced in the material of the ring member 11 by the forceps F. With the surgical staple in its generally stressed condition, the forceps F are manipulated to pierce the piercing projections 26, 27 into the skin S, as shown in FIGS. 6 and 9, with the surgical staple 10 in bridging relationship relationship to the wound W. When thus implanted, the forceps F are opened, withdrawn from the surgical staple 10 and the inherent induced forces in the surgical staple 10 automatically returns the surgical staple 10 to its generally unstressed condition (FIG. 7) drawing with it the margins M1, M2 of the wound W and thus closing the same (FIGS. 7 and 10).

The surgical staple 10 of FIG. 1 and 2 is of a preferred configuration since the pairs of relatively parallel portions 12, 13; 14. 15; 16, 17 and 18, 19 allow the ring member 11 to be gripped at different surface portions For example, the forceps F could be used to span the portions or surfaces 14, 15 or the surfaces or portions 18, 19 should it be necessary to do so to manipulate the surgical staple 10 for better access relative to the implantation procedure.

The surgical staple 10 need not have such parallel portions and, for example, may be of an elongated nature in the form of a generally oval shaped ring, as shown in FIGS. 3 and 4. The surgical staple 30 of FIGS. 3 and 4 in its unstressed configuration is similarly formed as a ring or ring member 3 which is also generally uniplanar (FIG. 4) and is defined by two relatively long portions 32, 33 which open toward each other and two relatively short curved portions 34, 35 which also open slightly toward each other. The portions 34, 35 carry respective piercing projections 36, 37 and the portions 32, 33 have respective loops 38, 39. The loops 38, 39 can be eliminated, if desired, to correspond the medial portion of the staple 30 generally to the portions 12, 13 of the staple 10. In the absence of the loops 38, 39, the legs L1, L2 of the forceps F are applied to the portions or surfaces 32, 33 to stress the ring member 31 and space the piercing projections 36, 37 away from each other a distance greater than the unstressed condition shown in FIGS. 3 and 4. However, since the portions 32, 33 are closer to each other in the unstressed condition of the surgical staple 30, as compared to the portions 12, 13 of the surgical staple 10, the piercing projections 36, 37 will move away from each other a lesser distance than possible in the surgical staple 10. In lieu of using the forceps F when the staple 30 is provided with the loops 38, 39, a tool, such as a tool T of FIGS. 13 and 14, is utilized. Though not illustrated, this tool has legs which are inserted into the loops 38, 39, the legs of the tool are squeezed, and this in turn brings the portions 32, 33 toward each other to increase the distance between the projections 36, 37. The staple 30 can then be manipulated in the manner heretofore described relative to FIGS. 5-8 to close an associated wound W. In this case the length of the surgical staple 30 is longer than the surgical staple 10 and affords advantages of implantation. However, both surgical staples 10, 30 are similar by providing an open area within the loop or body 11, 31, respectively, so that suturing can take place in this area. For example, in the case of a severe wound W, the staples 10, 30 can be used as a temporary closing device so that smaller suturing can take place within the area encompassed by the bodies 11, 31. Accordingly, the particular open and oval configuration of the surgical staples 10, 30 may be varied in keeping with this invention, but the characteristic which must be retained is the ability of the staple to be stressed by applied forces, implanted, and inherently returned to an unstressed condition to achieve wound closure.

Reference is now made to FIGS. 11 and 12 of the drawings which illustrates another surgical staple 40 formed as an elongated member 41 of flat surgical steel or plastic material which has a concavo-convex configuration and struck therefrom are a pair of skin piercing projections 36, 37 adjacent respective aperture means 35, 38. In the unstressed condition (FIGS. 11 and 12) the projections 36, 37 are spaced a distance D1 from each other. In order to close an open wound W of FIG. 13, legs L3, L4 of a tool T having a coil C are inserted in the respective apertures or openings 35, 38. The legs L3, L4 are normally spaced from each other the wider distance shown in FIG. 14, and incident to implantation, the tool T is squeezed to compress the coil C to bring the legs L3, L4 closer to each other. The legs L3, L4 are essentially squeezed together until they fit into the holes 35, 38 of the unstressed member 41 (FIGS. 11 and 12) after which the legs L3, L4 are released causing the coil C of the tool T to stress the member 41 and lengthen the distance between the projections 36, 37 (FIG. 13). When the skin piercing projections 36, 37 have been thus further spaced from each other than the distance D1, they are pushed into the skin S (FIG. 13), the legs L3, L4 of the tool T are then slightly squeezed, the tool is withdrawn (FIG. 14), and the stressed member automatically moves toward its unstressed condition (FIG. 14) closing the wound W.

Another surgical staple 50 (FIGS. 15 and 16) is constructed from a rod of surgical steel or similar material which is bent to form a generally S-shaped member 51. The member 51 includes a slightly curved or arcuate medial portion 52, opposite looped or loop ends 53, 54 and a skin piercing projection 56, 57 associated with each. The S-shaped member 51 lies generally in a common plane (FIG. 16) from which the skin piercing projections 56, 57 normally project The projections 56, 57 are similarly spaced a distance D1 from each other in the unstressed condition (FIGS. 15 and 16) of the surgical staple 50.

The tool T of FIGS. 13 and 14 can be used to implant the surgical staple 50. The legs L3, L4 are squeezed and inserted into the loops 53, 54, as indicated by the legs L3, L4 shown in cross section in FIG. 15. When the legs L3, L4 are slightly released the force of the coil C of the tool T straightens the medial portion 52 and slightly expands the loop portions 53, 54. The latter increases the distance D1 between the unstressed skin piercing projections 56, 57 and allows the surgeon to pierce the skin S with the medial portion 52 in bridging relationship to the wound W (FIG. 17). When the legs L3, L4 are removed (FIG. 18) the natural rebound characteristics of the material causes the surgical staple 52 to return to its original configuration (FIG. 18) closing the wound W.

Another surgical staple constructed in accordance with this invention is illustrated in FIGS. 21 and 22 of the drawings and is generally designated by the reference numeral 60. The surgical staple 60 is a generally cross-shaped member 61 formed of surgical steel or similar material having a loop 62, a pair of crossed legs 63, 84, and skin piercing projections 66, 67, respectively. In the normal unstressed condition of the surgical staple 80, the skin piercing projections 66, 67 are spaced from each other a distance D1. However, legs L1, L2 (FIG. 21) of the forceps are placed against opposite surfaces of the loop 62 and squeezed to constrict or close the loop 62 which automatically spaces the skin piercing projections 66, 67 a greater distance D2 (FIG.

23) from each other. In this condition the skin S is pierced (FIG. 23) with the surgical staple 60 in bridging relationship to the wound W. Upon removal of the forcep legs L1, L2, the spring-back characteristics of the surgical staple 60 inherently draw the projections 66, 67 toward each other closing the wound W (FIG. 24).

The surgical staples thus far described offer immense advantages, particularly because each staple design allows a variable degree of force to be applied thereto which in turn is applied to the wound margins during closure depending upon the placement of the staple relative to the wound at closure. For example, if a slight force is applied to bring the portions 12, 13 of the surgical staple 10 toward each other, a corresponding slight force is created during implant to draw the skin piercing projections 26, 27 toward each other after implant which in turn imparts a slight force to the skin itself. Obviously, if the skin S were prone to tearing because the tissue was very thin, a very slight force is highly advantageous. If, however, the skin was less susceptible to tearing, a greater force could be applied to the portions 12, 13 of the surgical staple 10 thus permitting greater force application to the piercing projections 26, 27 and to the skin itself. Thus, by varying the amount of force applied to the surgical staples prior to placement (or by the variation of the amount of the wound gap between the wound margins) one can vary the force applied to the wound to obtain the desired closure thereof. Thus, all the staples of the present invention offer the ability to vary wound closure from light approximation in cosmetic circumstances to tight approximation in high stress wounds. Each of the surgical staples also has been described by placing the piercing points simultaneously into the skin. An alternative method for placement involves first inserting only one of the skin piercing projections into the skin, using this hooking action to draw the hooked tissue or skin margin toward the second skin margin by manipulating the implantation tool, and after the two margins have been aligned, inserting the second skin piercing projection into the skin. Upon release of the staple the remaining necessary tension therein keeps the staple in place and the wound margins well approximated. In addition to permitting greater control of tissue margin alignment, this method also permits the use of a greater arc of curvature of the skin piercing projections which, while not essential, is beneficial in fixing certain tissues. This method also allows one-handed tissue closure without the need for a surgical assistant to help approximate wound margins. Similarly, such easy removal offers significant benefits intraoperatively when initial staple placement has been judged inadequate. Prior staples have required a separate tool for removal of the staple which was then discarded. The current invention allows use of the same placement tool for removal of a staple, the reuse of the misplaced staple, and the ability to alter the position of each piercing projection independently should only one be misapproximated, i.e., only one half of the staple would need to be removed and replaced.

It should also be noted that surgical staples can be removed as simply as implanted and with the same tools. For example, surgical forceps could be applied to the surgical staple 10 in FIG. 10 after the wound has healed, for example, squeezed and lifted simultaneously, and the piercing projections 26, 27 would be automatically progressively spaced from each other during the lifting of the surgical staple away from the skin S. In this fashion the staples could be removed virtually pain-free. The generally uniplanar configuration of each of the staples 10, 30, 40, 50 and 60 is an extremely important aspect of the invention because it allows each of the surgical staples, when implanted, to lie extremely close to or contiguous the skin, as is perhaps best illustrated in FIGS. 19 and 20. By lying flat against the skin the surgical staples cannot be accidentally dislodged and are unobtrusive. This advantage applies even to the slightly concave surgical staples, such as the staples 10 and 14, which have been illustrated highly exaggerated in their concavo-convex curvature for description purposes. In actual practice, however, the gap shown in FIG. 14 between the implanted staple 40 and the wound W would be virtually nonexistent.

Although a preferred embodiment of the invention has been specifically illustrated and described herein, it is to be understood that minor variations may be made in the apparatus and the method without departing from the spirit and scope of the invention as defined in the appended claims.

I claim:

1. A surgical staple comprising a generally closed loop planar member formed of relatively resilient material possessing inherent spring-back characteristics; said generally closed loop planar member having opposite surfaces and a pair of skin piercing projections projecting transversely away from one of said opposite surfaces and generally toward each other at generally opposite ends of said generally closed loop member; said pair of skin piercing projections being spaced from each other a first predetermined linear distance in a generally unstressed, neutral, operative condition of said staple; said skin piercing projections being spaced from each other a second predetermined linear distance greater than said first predetermined linear distance in a generally stressed, force-induced inoperative condition of said staple; and said generally closed loop planar member having spaced surface means against which forces are applied for transforming said generally planar member from its generally unstressed condition to its generally stressed condition whereby said piercing projections can be pierced into the skin on opposite sides of a wound and upon cessation of such applied forces said generally planar member automatically returns to its generally unstressed condition to automatically draw opposite margins of the wound toward each other.

2. The surgical staple as defined in claim 1 wherein said spaced surface means are opposite outer peripheral edge portions of said generally closed loop planar member.

3. The surgical staple as defined in claim 1 wherein said spaced surface means are edge portions located within an outer periphery of said generally closed loop planar member.

4. The surgical staple as defined in claim 1 wherein said closed loop member includes a peripheral outer edge, and said spaced surface means are opposite transversely spaced peripheral edge portions of said peripheral outer edge.

5. The surgical staple as defined in claim 1 wherein said closed loop member includes a peripheral outer edge, and said spaced surface means are opposite longitudinally spaced peripheral edge portions of said peripheral outer edge.

6. The surgical staple as defined in claim 1 wherein said closed loop member includes a peripheral outer edge, said spaced surface means are opposite transversely spaced peripheral edge portions of said peripheral outer edge, and said transversely spaced peripheral edge portions are spaced further from each other in said generally unstressed condition than in said generally stressed condition.

7. The surgical staple as defined in claim 1 wherein said closed loop member includes a peripheral outer edge, said spaced surface means are opposite longitudinally spaced peripheral edge portions of said peripheral outer edge, and said longitudinally spaced peripheral edge portions are spaced further from each other in said generally unstressed condition than in said generally stressed condition.

8. The surgical staple as defined in claim 1 wherein said closed loop member is a generally thin elongated rod.

9. The surgical staple as defined in claim 1 wherein said closed loop member is a generally thin elongated rod of a generally oval-shaped configuration.

10. The surgical staple as defined in claim 1 wherein said closed loop member has a pair of crossing leg portions each terminating at one of said projections.

11. The surgical staple as defined in claim 1 wherein said closed loop member is a generally thin elongated rod having a pair of spaced loop portions.

12. The surgical staple as defined in claim 1 wherein said closed loop member is a generally thin elongated rod having a pair of spaced loop portions and each loop portion terminating at one of said projections.

* * * * *